(12) United States Patent
Ha et al.

(10) Patent No.: US 7,262,324 B2
(45) Date of Patent: *Aug. 28, 2007

(54) METHOD OF PRODUCING UNSATURATED ACID IN FIXED-BED CATALYTIC PARTIAL OXIDATION REACTOR WITH ENHANCED HEAT CONTROL SYSTEM

(75) Inventors: Kyoung Su Ha, Deajeon (KR); Geon Yong Kim, Gwangju (KR); Seong Pil Kang, Daejeon (KR); Boo Gon Woo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 189 days.

This patent is subject to a terminal disclaimer.

(21) Appl. No.: 11/019,363

(22) Filed: Dec. 23, 2004

(65) Prior Publication Data

US 2005/0143601 A1 Jun. 30, 2005

(30) Foreign Application Priority Data

Dec. 24, 2003 (KR) ...................... 10-2003-0096476

(51) Int. Cl.
*C07C 51/16* (2006.01)
*B01J 8/04* (2006.01)

(52) U.S. Cl. ...................... 562/545; 422/197
(58) Field of Classification Search ...................... None
See application file for complete search history.

(56) References Cited

U.S. PATENT DOCUMENTS

| 3,147,084 A | 9/1964 | Franzen et al. |
|---|---|---|
| 3,801,634 A | 4/1974 | Engelbach et al. |
| 3,871,445 A | 3/1975 | Gutlhuber et al. |
| 4,256,783 A | 3/1981 | Sato et al. |
| 5,198,581 A | 3/1993 | Kawajiri et al. |
| 5,739,391 A | 4/1998 | Ruppel et al. |
| 6,069,271 A | 5/2000 | Tanimoto et al. |

FOREIGN PATENT DOCUMENTS

| JP | 11-080052 A | 3/1999 |
|---|---|---|
| JP | 2001-129384 A | 5/2001 |
| JP | 2001-137689 A | 5/2001 |
| JP | 2001-139499 A | 5/2001 |
| KR | 10-0407030 B | 3/2004 |
| WO | WO-2004/007064 A1 | 1/2004 |

*Primary Examiner*—Sikarl A. Witherspoon
(74) *Attorney, Agent, or Firm*—Birch, Stewart, Kolasch & Birch, LLP (57) ABSTRACT

The present invention provides a process of producing unsaturated acids from unsaturated aldehydes by fixed-bed catalytic partial oxidation in a shell-and-tube heat exchanger-type reactor, as well as a shell-and-tube heat exchanger-type reactor for use in the process. In the invention, second-stage reaction zone of mainly producing unsaturated acids by the catalytic vapor phase oxidation of an unsaturated aldehyde-containing gas mixture produced in a first-stage reaction zone with molecular oxygen is divided into two or more shell spaces by at least one partition. Each of the divided shell spaces is filled with a heat transfer medium, and the heat transfer medium in each shell space is maintained at isothermal temperature or a temperature difference of 0-5° C. Also, in order to protect catalyst layers from a highly exothermic reaction, the process is performed at a limited temperature difference between the temperature at a hot spot and the temperature of the heat transfer medium. Also, in order to facilitate the removal of heat generation at a location where the partition is placed, a reaction inhibition layer is disposed in that location. The improved heat control system for reactors provided according to the present invention can secure the heat stability of the catalyst layer, reduce the amount of byproducts, and increase the yield of a final product.

21 Claims, 2 Drawing Sheets

METHOD OF PRODUCING UNSATURATED ACID IN FIXED-BED CATALYTIC PARTIAL OXIDATION REACTOR WITH ENHANCED HEAT CONTROL SYSTEM

TECHNICAL FIELD

The present invention relates to a process of producing unsaturated acids from unsaturated aldehydes, particularly a process of producing acrylic acid from acrolein, by the catalytic vapor phase oxidation, as well as a fixed bed shell-and-tube heat exchanger-type reactor for use in this process.

BACKGROUND ART

A process of producing unsaturated aldehydes and unsaturated acids from olefins corresponds to typical catalytic vapor phase oxidation.

Generally, catalytic vapor phase oxidation is carried out by charging one or more kinds of granular catalysts into a reactor tube (catalytic tube), supplying feed gas into a reactor through a pipe, and contacting the feed gas with the catalyst in the reactor tube. Reaction heat generated during the reaction is removed by heat exchange with a heat transfer medium whose temperature is maintained at a predetermined temperature. The heat transfer medium for heat exchange is provided on the outer surface of the catalytic tube so as to perform heat transfer. The mixture containing the desired product is collected, recovered and sent to a purification step through a pipe. Since the catalytic vapor phase oxidation is a highly exothermic reaction, it is very important to control the reaction temperature in a certain range and to reduce the size of the temperature peak at a hot spot occurring in a reaction zone.

The partial oxidation of olefin uses a multimetal oxide containing molybdenum and bismuth or vanadium or a mixture thereof, as a catalyst. Typical examples thereof include a process for the production of acrolein or acrylic acid by the oxidation of propylene, a process for the production of phthalic anhydride by the partial oxidation of naphthalene or orthoxylene, and a process for the production of maleic anhydride by the partial oxidation of benzene, butylene or butadiene.

Generally, acrylic acid, a final product, is produced from propylene by a two-stage process of vapor phase catalytic partial oxidation. In a first stage, propylene is oxidized by oxygen, dilution inert gas, steam and a certain amount of a catalyst, so as to mainly produce acrolein, and in a second stage, the produced acrolein is oxidized by oxygen, inert dilution gas, steam and a certain amount of a catalyst, so as to produce acrylic acid. The catalyst used in the first stage is a Mo—Bi-based oxidation catalyst which oxidizes propylene to mainly produce acrolein. Also, some acrolein is continuously oxidized on such a catalyst to produce acrylic acid. The catalyst used in the second stage is a Mo—V-based oxidation catalyst, which oxidizes mainly acrolein in acrolein-containing gas mixture produced in the first-stage, thus mainly producing acrylic acid.

A reactor for performing such a process is provided either in such a manner that both the two-stages can be performed in one catalytic tube or in such a manner that the two stages can be performed in different catalytic tubes (see U.S. Pat. No. 4,256,783).

Meanwhile, acrylic acid manufacturers now conduct diversified efforts to improve the structure of such a reactor, or to propose the most suitable catalyst to induce oxidation, or to improve process operations, so as to increase the production of acrylic acid by the reactor.

In part of such prior efforts, propylene which is supplied into the reactor is used at high space velocity or high concentration. In this case, there are problems in that rapid oxidation in the reactor occurs, making it difficult to control the resulting reaction temperature, and also a high temperature at hot spot in the catalyst layer of the reactor and a heat accumulation around the hot spot are produced, resulting in an increase in the production of byproducts, such as carbon monoxide, carbon dioxide and acetic acid, thus reducing the yield of acrylic acid.

Furthermore, in the case of producing acrylic acid using a high space velocity and high concentration of propylene, as an abnormal increase in temperature occurs in the reactor, various problems, such as the loss of active ingredients from the catalyst layer, a reduction in the number of active sites caused by the sintering of metal components, are caused, thus deteriorating the function of the catalyst layer.

Accordingly, in the production of acrylic acid, the control of the heat of reaction in the relevant reactor is important of all things. Particularly, not only the formation of hot spots in the catalyst layer but also the accumulation of heat around the hot spot must be inhibited, and the reactor must be effectively controlled such that the hot spots do not lead to reactor runaway (a state where the reactor is not controlled or explodes by a highly exothermic reaction).

Thus, it is very important to inhibit hot spots and heat accumulation around the hot spot so as to extend the life cycle of a catalyst and inhibit side reactions, thus increasing the yield of a product such as acrylic acid. To achieve this inhibition, various attempts have been steadily made.

A fundamental method is to form several catalyst layers having activities that vary according to the moving direction of reactants (hereinafter, referred to as the "axial direction"). Namely, at a reactor inlet side where hot spots generate, a catalytic layer with low activity is formed, and catalyst layers whose activities increase slowly toward a reactor outlet side are formed. Typical methods for controlling catalytic activity include: a method of making catalytic particles by mixing a catalytic material with inactive materials (e.g., U.S. Pat. No. 3,801,634, Japanese patent No. 53-30688B, and Japanese patent No. 63-38831); a method of controlling activity and selectivity by either changing the kind of alkali metals and controlling the amount thereof (e.g., U.S. Pat. No. 6,563,000); a method of controlling activity by adjusting the occupied volume of catalytic particles (e.g., U.S. Pat. No. 5,719,318); and a method for controlling activity by controlling sintering temperature in the preparation of a catalyst (e.g., U.S. Pat. No. 6,028,220). However, such methods have some effects but still need to be improved.

Furthermore, in order to more effectively use the above-mentioned technologies, a reactor system needs to be designed such that it is suitable for oxidation with excessive heat generation. Particularly, in order to inhibit the inactivation of a catalyst caused by excessive heat generation, it is necessary to establish an efficient heat control system capable of controlling excessively high peak temperature at hot spots, thermal accumulation around the hot spot and runaway. For the establishment of the efficient heat control system, studies have been performed on the introduction of a perforated shield plate (e.g., U.S. Pat. No. 4,256,783, European patent No. 293224A, and Japanese patent No. 52-83936), the establishment of circulation pathway of molten salts by the placement of various baffles (e.g., U.S. Pat. No. 3,871,445), the design of an oxidation reactor integrated with a cooling heat exchanger (e.g., U.S. Pat. No. 3,147,084), a multi-stage heat control structure using an improved heat exchanger system (e.g., Korean patent application No. 10-2002-40043, and PCT/KR02/02074), etc.

DISCLOSURE OF THE INVENTION

As described above, since the catalytic vapor phase oxidation not only progresses at high temperature but also is an exothermic reaction which has excessive heat generation, it can cause a reduction in selectivity due to the generation of a hot spot with very high temperature around a reactor inlet or the heat accumulation around the hot spot, and also can result in a significant reduction in the performance of a catalyst in a long-term viewpoint. Particularly, if the temperature of the hot spot is higher than the calcination temperature of the catalyst, the life cycle of the catalyst will be reduced to shorten the replacement time of the entire catalyst layers, resulting in an economical loss. In addition, if the activity of the filled catalyst layers is reduced and the temperature of a heat transfer medium (molten salt) is elevated in order to compensate for the reduction in activity, the temperature of a hot spot and the heat accumulation in the hot spot will also be increased, and as a result, a solution to solve this problem is required.

A catalyst for use in the second-stage reaction zone of mainly producing unsaturated acids from unsaturated aldehydes is generally calcinated in a temperature of 300-500° C. For this reason, when the maximum peak temperature of the catalyst layer is higher than the calcination temperature in the preparation thereof, the deterioration of the catalyst layer will occur, resulting in a reduction in yield. Accordingly, there is a need for a production process and reactor structure in which the catalyst layer is divided in a plurality of reaction spaces so that the peak temperature of each of the reaction zones can be controlled.

In addition, in the results of experiments conducted by the present inventors over several years, if a second-stage reactor filled with a highly active catalyst having an acrolein conversion of more than 95% is operated without independent temperature control along the axial direction, a hot spot close to the calcination temperature of the catalyst will occur at the first half of the catalyst layer.

The present inventors have made improvements in a fixed-bed shell-and-tube heat exchanger-type reactor of producing unsaturated aldehydes and unsaturated acids from olefins. In the improvements, a second-stage reaction zone of performing the catalytic vapor phase oxidation of an acrolein-containing gas mixture produced in a first-stage reaction zone was divided into two or more zones in an axial direction by at least one partition, and the temperature of a heat transfer medium filled in each of the divided shell spaces of the second-stage reaction zone was independently set to a temperature suitable for the activity of a catalyst and the degree of reaction. As a result of such improvements, the present inventors have found that a hot spot and heat accumulation around the hot spot could be inhibited. The present invention has been perfected based on this finding.

An object of the present invention is to provide a production process in which the temperature difference between the peak temperature of a catalyst layer in each of the divided reaction zones and the temperature of a heat transfer medium filled in the shell space corresponding to that zone is controlled, so that the process is not only thermally stable but also can be operated without a reduction in yield, even in the presence of a catalyst with very high activity, as well as an improved heat exchange-type reactor for use in this process.

Another object of the present invention is to provide a production process in which a reaction inhibition layer is inserted in order to facilitate the removal of heat generation at a location where the partition is placed, as well as a shell-and-tube heat exchanger-type reactor for use in this process.

In one aspect, the present invention provides a process of producing unsaturated acids from unsaturated aldehydes, particularly a process of producing acrylic acid from acrolein, by fixed-bed catalytic partial oxidation in a shell-and-tube heat exchanger-type reactor, the reactor comprising one or more catalytic tubes each including a reaction zone of producing the unsaturated acids, the improvement wherein: the reaction zone is divided into two or more shell spaces by at least one partition, each of the divided shell spaces being filled with a heat transfer medium, the heat transfer medium being maintained at isothermal temperature or a temperature difference of 0-5° C., in which the temperature difference between the temperature of the heat transfer medium and the temperature of a hot spot is limited, and/or a reaction inhibition layer is inserted into a location where the partition is placed.

In another aspect, the present invention provides a shell-and-tube heat exchanger-type reactor which can be used in a process of producing unsaturated aldehydes and unsaturated acids from olefins by fixed-bed catalytic partial oxidation, the reactor comprising one or more catalytic tubes each including a first-stage reaction zone of mainly producing the unsaturated aldehydes, a second-stage reaction zone of mainly producing the unsaturated acids, or both the two zones, the improvement wherein the second-stage reaction zone is divided into two or more shell spaces by at least one partition, each of the divided shell spaces being filled with a heat transfer medium, the heat transfer medium being maintained at isothermal temperature or at a temperature difference of 0-5° C., in which the temperature difference between the temperature of the heat transfer medium and the temperature of a hot spot is limited, and/or a reaction inhibition layer is inserted into a location where the partition is disposed.

As used herein, the term "divided shell spaces" indicates internal spaces surrounded by a catalytic tube, a shell, a partition, a tube sheet, etc.

1. Placement of Partition

Only with uniform circulation of a heat transfer medium in a reactor, the heat of catalytic vapor phase reaction cannot be satisfactorily controlled, and a great heat spot often occurs, thus causing excessive oxidation at a local place in the reactor. This results in an increase in undesirable combustion reactions, thus reducing the yield of the desired product. Furthermore, a catalyst is always exposed to high temperature caused by the hot spot so that the life cycle of the catalyst reduced.

Also, if the temperature of the heat transfer medium is changed continuously in the axial direction without a partition, excessive efforts will be required in order to remove reaction heat caused by catalytic oxidation or to inhibit heat accumulation, and it will be very difficult to exactly set the desired temperature profile. Moreover, the magnitude and location of the hot spot will vary depending on the kind and activity of a catalyst used.

Accordingly, considering the characteristic and reactivity of the catalyst, the present invention utilizes a heat control system in which a partition is used such that a hot spot and heat accumulation around the heat spot can be controlled and the generation of heat can be structurally controlled.

The location of the partition is preferably established based on the exact prediction of a position where a hot spot is formed.

In the present invention, the location of the partition is established by the characteristic analysis of temperature profile such that it includes at least one temperature peak. Thus, heat in a region with the problems of a hot spot and heat accumulation around the hot spot can be intensively controlled in an independent heat control space, and even the case where the characteristic of temperature profile is changed can be overcome with flexibility.

The hot spot where the highest temperature peak occurs is produced by the generation of reaction heat resulting from catalytic vapor phase oxidation, and determined by factors, such as the composition of reactants, the flow rate (L/min) of reactants, the temperature of a heat transfer medium, etc., and has a certain position and size in a certain process condition. However, when the activity of a catalyst changes with time, the location and temperature magnitude of the hot spot can change.

Each of catalyst layers generally has at least one hot spot. Portions of the second-stage reaction zone, which have the problem of heat control, are hot spots which are generated in the front portion of the second-stage oxidation catalyst layer, in which unsaturated aldehyde (acrolein), a main reactant, and molecular oxygen, are present at high concentrations. Also, if two or more catalyst layers are filled in the second-stage reaction zone, a hot spot can be generated around the boundary between the adjacent catalyst layers.

The partition is preferably located at either a position where a hot spot and heat accumulation caused by the hot spot become problems, or a position allowing the largest possible removal of heat generation in each zone.

2. Heat Transfer Medium

In the inventive production process and heat exchanger-type reactor, the temperatures of the heat transfer medium in each of the divided shell spaces are set as nearly as possible to isothermal conditions. The difference between the temperatures of the heat transfer medium at both the ends of a catalyst layer in each of the divided shell spaces preferably has a temperature difference of 0-5° C., and more preferably 0-3° C., depending on the amount of heat generation and the heat transfer capacity of the heat transfer medium.

The temperature difference between the heat transfer media in the adjacent shell spaces of the second-stage reaction zone is preferably set to 0-50° C., and more preferably 5-15° C., in an axial direction.

Examples of the heat transfer medium include very highly viscous media, for example a molten salt which consists mainly of a mixture of potassium nitrate and sodium nitrite. Other examples of the heat transfer medium include phenyl ether media (e.g., "Dowtherm"), polyphenyl media (e.g., "Therm S"), hot oil, naphthalene derivatives (S. K. oil) and mercury.

By controlling the flow rate of the heat transfer medium, a reaction in each of the shell spaces of the reactor can be carried out at substantially the same temperature of the heat transfer medium.

If the temperatures of the heat transfer medium filled in each of the divided shell spaces are set to change in the moving direction of reactants (hereafter, referred to as the "axial direction"), the reactivity of the catalyst layer will change in proportion to temperature magnitude.

By applying the multi-stage heat control system in which the partition is used and the temperature of the heat transfer medium is controlled, the present invention can provide a process of producing acrylic acid in an efficient and stable manner even in catalyst layers with the same size, shape and activity, as well as a reactor for use in this process.

The temperatures of the heat transfer medium (molten salt) in each of the divided shell spaces are preferably so set that a catalyst has the optimum activity.

In the present invention, in order to inhibit a hot spot and heat accumulation around the hot spot either in a catalytic tube for each reaction stage or in each reaction stage in one catalytic tube under high reactant concentration or high reactant space velocity, the temperatures of the heat transfer medium are changed in the axial direction so as to reduce catalyst damage caused by a highly exothermic reaction and to inhibit a reduction in yield caused by side reactions, resulting in an increase in yield.

The temperature control of the heat transfer medium in the axial direction is preferably performed in the following manner. The temperature profile of a catalyst layer is analyzed so as to quantitatively determine the location and peak magnitude of a hot spot. As a result of the analysis, in a divided reaction region where the hot spot occurs, the temperature of the heat transfer medium is set close to the lowest possible temperature for catalyst activation, and in other regions where thermal accumulation at the hot spot would not become a great problem, the temperature of the heat transfer medium is increased to the maximum temperature acceptable in the present invention so as to obtain the highest yield. Also, continuous feedback of the temperature profile analysis is performed so as to set process conditions to the optimum conditions.

Since a reactor front-portion with high unsaturated aldehyde concentration and high unsaturated aldehyde space velocity shows the highest activity, a hot spot of the highest temperature peak is formed in the reactor front-portion. It is preferable that the temperature of the heat transfer medium within a portion of the shell space, which corresponds to a location where this hot spot is formed, should be lowered to the lowest possible temperature for catalyst activation, such that the magnitude of the hot spot can be reduced and heat accumulation around the hot spot can be prevented while preventing significant reduction in catalyst reactivity.

According to one embodiment of the present invention, improvements are made in a process of producing unsaturated acid by reacting unsaturated aldehyde in the presence of a catalyst with molecular oxygen, dilute inert gas, steam, and optionally recycled off-gas which has not been absorbed into an absorbing column. In the improvements, the second-stage reaction zone of producing unsaturated acid from unsaturated aldehyde-containing gas is divided into two or more separate shell spaces in an axial direction, and the temperatures of a heat transfer medium filled in each of the shell spaces are set within the temperature difference range proposed in the present invention, so that the activity and reactivity of catalyst layers are suitably controlled.

In the second-stage reaction zone where acrylic acid is mainly produced from acrolein, the temperature of the catalyst layer with activity is about 260-360° C. and the temperature of the heat transfer medium is set to about 260-330° C. Here, in addition to acrylic acid, unreacted acrolein, carbon monoxide, carbon dioxide, steam, acetic acid, unreacted propylene and small amounts of byproducts are discharged through an outlet. Since the second-stage reaction is a reaction which progresses at high temperature and is highly exothermic, a heat of 60 kcal per g-mol of acrolein is generated and the temperature at a hot spot reaches 310-350° C.

For example, when a shell space corresponding to the second-stage reaction zone is divided into three independent spaces, two partitions will be disposed within the shell space in a perpendicular direction to the axis of the catalytic tube so as to provide a structure with three divided shell spaces where the temperatures of the heat transfer medium are independently controlled. In this case, the temperatures of the heat transfer medium filled in each of the divided shell spaces may be set to, for example, 310° C., 305° C. and 315° C., respectively, in a direction from an inlet to an outlet.

3. Control of Temperature of Heat Transfer Medium

The present invention is characterized in that the temperatures of the heat transfer medium in a plurality of the divided shell spaces are set in such a way that the temperatures are suited to the activity and reactivity of a catalyst. Namely, the temperatures of the heat transfer medium are so set that, when the shell spaces divided by the partitions in the second-stage reaction zone are named, such as zone 1, zone 2, zone 3, . . . and zone N in the axial direction, $T_{h1}$-$T_{salt1}$ is $\leq 130°$ C., and preferably $\leq 75°$ C., and $T_{hN}$-$T_{saltN}$ is $\leq 110°$ C., and preferably $\leq 70°$ C., wherein N is an integer of 2 or more.

Here, $T_{h1}$ is the peak temperature of a reaction mixture (the peak temperature of the catalyst layer) in a catalyst layer corresponding to the first shell space, and $T_{hN}$ is the peak temperature of a reaction mixture in a catalyst layer corresponding to the Nth shell space. And $T_{salt1}$ is the temperature of a heat transfer medium (molten salt) filled in the first shell space, and $T_{saltN}$ is the temperature of a heat transfer medium filled in the Nth shell space.

If the temperatures of the heat transfer medium in each of the shell spaces divided by the partition are set within the temperature difference range given as described above, the activity and reactivity of a catalyst can be suitably controlled so as to inhibit a hot spot and heat accumulation around the hot spot.

In the first shell space, the concentration and pressure of reactants are high, so that the temperature difference between the peak temperature of the catalyst layer and the temperature of the molten salt is higher than that in the next shell space. For this reason, the temperature difference range in the first shell space will be surely wider than that in the next shell space. However, the inventive method is a method by which the magnitude of peak temperature in the first shell space is minimized while a temperature difference in the next shell space is also limited to a certain range, so as to prevent local excessive heat generation, thus making the shape of temperature profile smooth. The limited temperature difference range is based on the result of various experiments conducted over several years by the present inventors.

If operations are done without this limited temperature difference range, the sintering of a catalyst in a hot spot, the loss of important metal components, an increase in byproducts, etc., can be caused, and particularly accidents can also occur due to a sudden exothermic reaction occurring when introducing raw materials into a reactor. For these reasons, the inventive method is technologically necessary for safe start-ups and stable operations.

4. Reaction Inhibition Layer

The number of catalytic tubes in a commercial shell-and-tube reactor of producing unsaturated acid such as acrylic acid reaches several thousands to several tens of thousands, and a partition disposed in the reactor has a very large thickness of 50-100 mm. Thus, if the second-stage reaction zone is divided into two or more shell spaces, the removal of heat generation caused by a reaction in the position where the partition is disposed will not be easy, thus causing a problem in heat transfer.

To eliminate such a problem, the present invention has another characteristic in that a layer made of an inactive material alone or a mixture of an inactive material and a catalytic material, i.e., a reaction inhibition layer is provided within a portion of the catalytic tube, which corresponds to a position where the partition is disposed.

Such a reaction inhibition layer is a layer with different characters from an inactive layer which is filled between the first-stage reaction zone and the second-stage reaction zone to a height of about 400-1,000 mm so as to induce cooling to a reaction temperature suitable for the second-stage reaction. This reaction inhibition layer is a filling layer for minimizing heat generation in a position with the problem of heat transfer.

The volume ratio of an inactive material to a catalytic material in this reaction inhibition layer is preferably 20-100%, and more preferably 80-100%. The filling height of the reaction inhibition layer is 20-500%, and preferably 120-150%, relative to the thickness of the partition, indicating that the reaction inhibition layer completely overlaps the thickness of the partition. However, if the height of the reaction inhibition layer must be made smaller than the thickness of the partition, the reaction inhibition layer will preferably be filled in such a manner that the largest possible area overlaps.

The inactive material used in the reaction inhibition layer is designated as a material which is inactive to a reaction of producing unsaturated acids from olefins or unsaturated aldehydes, for example, a catalytic oxidation reaction of propylene or acrolein. It can be used in a sphere, cylinder, ring, rod, plate or wire mesh shape, or a mass shape with suitable size, or a suitable combination thereof. Widely known examples of the inactive material include alumina, silica alumina, stainless steel, iron, steatite, porcelain, various ceramics, and mixtures thereof.

5. Structure of Catalyst Layer

The catalyst tubes in the reactor include at least one catalyst layer made of oxidation catalyst particles for each of the two reaction zones.

The catalyst layer in the second-stage reaction zone may be made of either one layer whose activity is uniform in the axial direction, or made of at least two layers stacked in a direction along which the catalyst activity increases. This is likewise applied to the catalyst layer in the first-stage reaction zone.

6. Reactor Structure and Reaction Procedure

Regarding the structure of a reactor according to the present invention, the shell space in the second-stage reaction zone is divided into at least two shell spaces by the partition, such that the temperatures of the heat transfer medium filled in each of the divided shell spaces can be independently controlled. The temperatures of the heat transfer medium filled in each of the divided shell spaces are so set that they are suited to the activity and reactivity of a catalyst.

Figure 1:
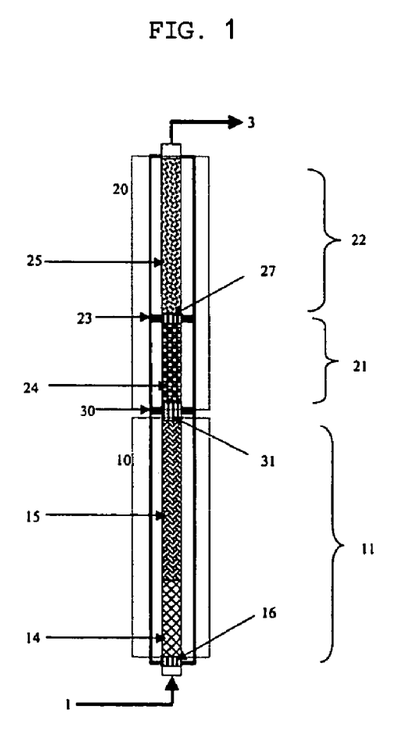
FIG. 1 is a schematic diagram showing the structure of catalyst layers and the location of a partition in a pilot reactor in which first-stage reaction and second-stage reaction are successively performed in one catalytic tube. A partition is placed at a boundary between the catalyst layers in the second-stage reaction zone.
Figure 2:
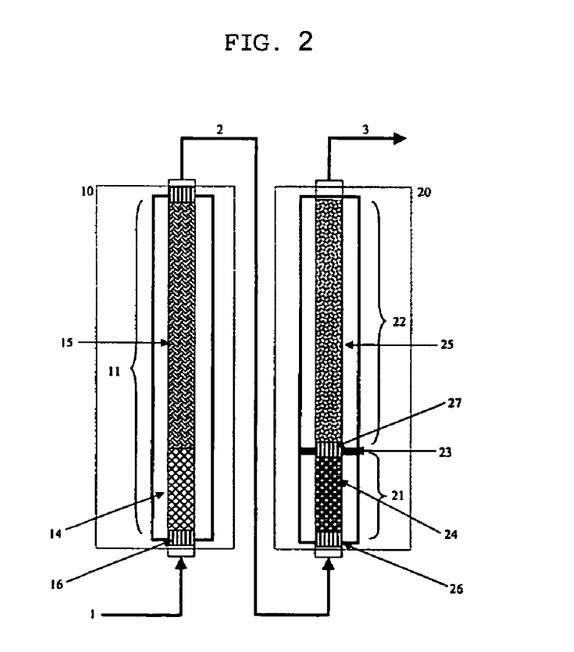
FIG. 2 is a schematic diagram showing the structure of a pilot reactor consisting of two catalytic tubes, and the structure of catalyst layers and the location of a partition in each of the catalytic tubes. First-stage reaction and second-stage reaction are conducted in the two catalytic tubes, respectively, and a partition is placed at a boundary between the catalyst layers in the second-stage reactor.
Figure 3:
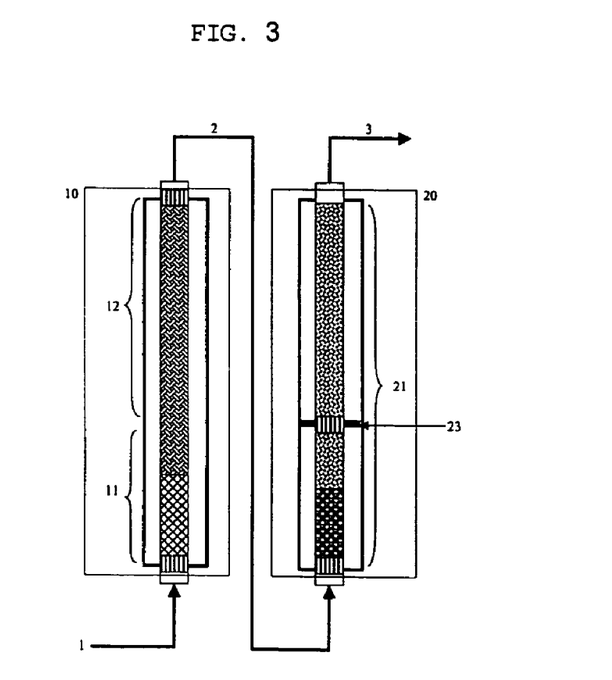
FIG. 3 is a schematic diagram showing the structure of a pilot reactor consisting of two catalytic tubes, and the structure of catalyst layers and the location of a partition in each of the catalytic tubes. First-stage reaction and second-stage reaction are conducted in the two catalytic tubes, respectively, and a partition is not placed at a boundary between the catalyst layers in the second-stage reactor.
Figure 4:
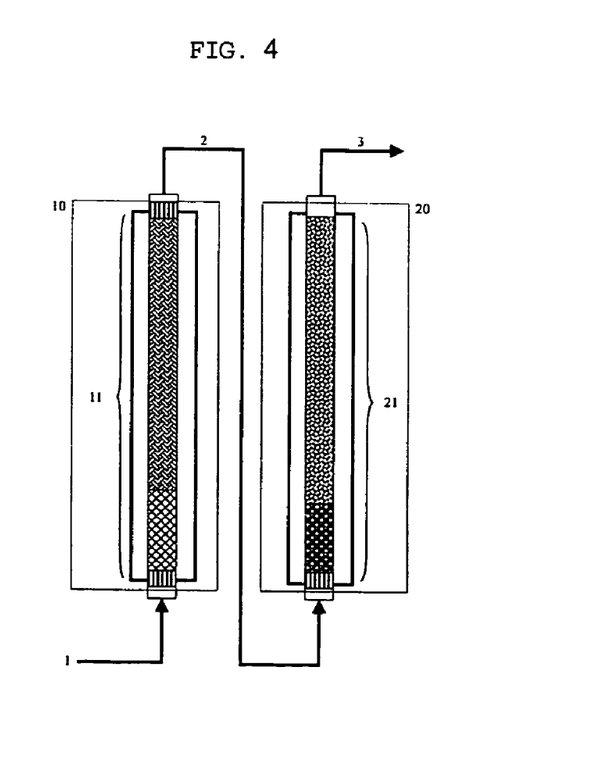
FIG. 4 is a schematic diagram showing the structure of a pilot reactor consisting of two catalytic tubes, and the structure of catalyst layers in the catalytic tubes. First-stage reaction and second-stage reaction are conducted in the two catalytic tubes, respectively, and a partition is not disposed in the pilot reactor.

FIGS. 1 to 3 show a pilot structure designed to transfer the idea of the present invention, and the scope of the present invention is not limited only to details shown in the drawings.

It is well known that an actual shell-and-tube heat exchanger-type reactor can be represented by one catalytic tube reactor with respect to reactor behavior characteristics, such as temperature, yield, etc. Thus, the effects of the present invention will now be described by a pilot experiment where one catalytic tube is disposed in each reaction stage.

For the description below, a catalyst layer for a second-stage reaction is named as follows, and the following sequence coincides with a reaction pathway:

The first catalyst layer in the second-stage reaction: a second stage-layer A;

The second catalyst layer in the second-stage reaction: a second stage-layer B;

The third catalyst layer in the second-stage reaction: a second stage-layer C;

If necessary, the catalyst layers may be disposed in such a manner that their catalytic activity gradually increases toward the layers A, B, C, . . . .

FIG. 1 shows the structure of a pilot reactor structured such that two-stage reaction occurs in one catalytic tube. As shown in FIG. 1, a first-stage reaction zone 10 and a second-stage reaction zone 20 are connected in series with each other, such that reactants fed into a reactor inlet are subjected to first-stage reaction and then to second-stage reaction, thus producing acrylic acid. If necessary, two or more catalyst layers with different activities (excluding an inactive material layer and a reaction inhibition layer) can be included in each of the reaction zones.

Hereinafter, a reaction system in which two catalyst layers with different activities are placed in each reaction stage will be described by way of example.

In FIG. 1, reference numerals 11, 21 and 22 denote shell spaces (jackets) into which heat transfer media with different temperatures are filled. FIG. 1 shows the structure of the catalyst layers in the catalytic tube, and the following layers are filled in the catalytic tube in an order from the lower level to the upper level:

Inactive particle-layer A 16
First-stage reaction zone:
First stage-layer A 14
First stage-layer B 15
Inactive particle-layer B 31
Second-stage reaction zone:
Second stage-layer A 24
Second stage-reaction inhibition layer 27
Second stage-layer B 25

The first stage-layer A and the first stage-layer B can be filled with catalyst layers with the same or different activities. The second stage-layer A and the second stage-layer B can be filled with catalyst layers with the same or different activities. Between the first-stage reaction zone and the second-stage reaction zone, inactive particles (inactive particle-layer B) are suitably filled such that the temperature of a reaction mixture entering the second stage is in the range of activation temperature of second stage-layer A. The shell space in the second-stage reactor is divided into two heat control spaces which are heat-controlled independently. As shown in FIG. 1, a partition 23 in the second-stage reaction zone is located at a boundary between the catalyst layers. Reference numeral 30 in FIG. 1 denotes a partition of providing a division between the first-stage and second-stage reaction zones, and the inactive material layer 31 is a filling layer of bring the temperature of reactants to a temperature suitable for the catalyst layer 24 in the second-stage reaction zone.

Reference numeral 1 in FIG. 1 denotes the flow of reactants consisting of propylene, molecular oxygen, dilute gas, and steam. Reference numeral 3 in FIG. 1 denotes the flow of products consisting of main product acrylic acid, dilute gas, molecular oxygen, unreacted propylene, unreacted acrolein, and small amounts of byproducts, etc. Into the second-stage reaction zone according to the present invention, acrolein-containing gas mixture passed through the first-stage reaction zone (gas mixture just after the first stage-layer B) is fed which consists of acrolein as a main feed material, dilute gas, molecular oxygen, unreacted propylene, acrylic acid, carbon monoxide, carbon dioxide, and small amounts of byproducts.

Reference numerals 21 and 22 in FIG. 1 denote two divided shell spaces (jackets) in the second-stage reaction zone, and reference numeral 11 in FIG. 1 denotes a shell space (jacket) in the first-stage reaction zone.

FIG. 2 shows the structure of a pilot reactor in which a first-stage reaction zone and a second-stage reaction zone are separated in two catalytic tubes, respectively. In FIG. 2, the fundamental structure of the reactor, and the structure of the catalyst layers, are the same as those in FIG. 1.

FIG. 3 shows a structure where two or more catalyst layers with different activities are filled in each of the reaction zones. In this structure, a partition is placed away from a boundary between the catalyst layers. Also, this structure can be used when the first heat control zone is defined by a section ranging from a second-stage reactor inlet to the peak temperature zone of the second stage-layer B, and the second heat control zone is defined by the remaining section. Also, this structure can be applied when two or more adjacent temperature peaks are present in the catalyst layer so that such temperature peaks need to be controlled at the same time using one shell space (jacket).

For example, peak temperatures occurring in the second stage-layer A and the second stage-layer B can be controlled below a pre-determined peak temperature of catalyst layers to be managed, by controlling the temperatures of heat transfer medium filled of the first heat control zone. In FIG. 3, a method of positioning the partition, and a method of filling the catalyst and the inactive material, are the same as those in FIG. 1.

In the location of the partition, a first partition can be disposed between the preceding catalyst layer and the relevant catalyst layer in the filling order, and a second partition can be disposed following the peak position of the relevant catalyst layer. If the relevant catalyst layer is a first catalyst layer either at a reactor inlet or at the initiation point of the second-stage reaction zone, one partition will be disposed following the peak position of the relevant catalyst layer. The shell spaces divided by the partition may include the position of one or more peak temperatures occurring in a plurality of the catalyst layers.

The inventive heat control system can be applied in the oxidation of olefins, and also in a reaction system where the kind of reaction varies in the axial direction so that it is carried out for each stage, as well as a system where reaction temperature must be changed according to each reaction zone so that it is controlled at the optimal temperature.

MODE FOR CARRYING OUT THE INVENTION

Hereinafter, the present invention will be illustrated by way of the following examples which are not construed to limit the scope of the present invention.

Example 1

(Improved Heat Control System): Changes in Yield and Magnitudes of Temperature Peaks at Hot Spots with Change in Setting Temperature of Molten Salt As shown in FIG. 1, a pilot reactor was provided in which first-stage reaction and second-stage reaction are conducted in a catalytic tube. The catalytic tubes was 26 mm in inner diameter, and the catalytic tube corresponding the second-stage reaction zone was filled with catalyst layers with a height of about 2670 mm. Reference numerals 21 and 22 in FIG. 1 denote the divided shell spaces of the second-stage reaction zone. The temperatures of molten salts filled in the shell spaces were set to 285° C. and 270° C., respectively. The two catalyst layers filled in the first-stage reaction zone 10 as shown in FIG. 1 were made of a catalyst based on molybdenum (Mo) and bismuth (Bi), the preparation of which is described in Korean patent No. 0349602 (Application No. 10-1997-0045132). The two catalyst layers filled in the second-stage reaction zone 20 were made of a catalyst based on molybdenum and vanadium (V), the preparation of which is described in Korean patent No. 0204728 or Korean patent No. 0204729.

The second-stage reaction zone was filled with two catalyst layers whose activity increases from an inlet to an outlet, according to a method for controlling catalytic activity as disclosed in U.S. Pat. Nos. 3,801,634 and 4,837,360. The activity of the first catalyst layer is about 87% of the second catalyst.

The second-stage reaction zone was filled with two catalyst layers having heights of 700 mm and 1970 mm, respectively, in an axial direction. The location of a partition in the second-stage reaction zone was 700 mm away from the initiation point of the catalyst layers. This partition was disposed based on the results of experimental studies conducted by the present inventors over several years, which revealed that a hot spot was generally generated before locations 1000 mm away from the initiation point of the catalyst layers, and 700 mm away from the initiation portion under the experimental conditions of Example 1. In a portion inside the catalytic tube corresponding to the location of the partition, an inactive material layer was filled to a thickness corresponding 120% of the thickness of the partition. An acrolein-containing gas mixture including acrolein, acrylic acid, oxygen, steam, inert gas, carbon monoxide, carbon dioxide and other byproducts, which has been produced from the first-stage reaction zone, was fed into the second-stage reaction region, passed through a reaction pathway and then discharged through an outlet 3. The starting materials fed into the second-stage reaction zone was comprised of 5.5% of acrolein, 0.9% of acrylic acid, 5.0% of oxygen, 1.0% of byproducts such as $CO_x$ and acetic acid, and the remaining amount of nitrogen gas. Space velocity in the second-stage reaction zone was 1500 $hr^{-1}$ (STP) (standard temperature and pressure). Also, the space velocity of acrolein (reaction hydrocarbon) entering the second-stage reaction zone was 81 $hr^{-1}$ (STP), and the pressure of the fed gas mixture was 0.6 $kgf/cm^2G$.

$T_{h1}$-$T_{salt1}$ was 46.2° C., and $T_{h2}$-$T_{salt2}$ was 39.9° C.

In the second-stage reaction zone, the peak temperature at a hot spot was 331.2° C., and the yield of acrylic acid was 84.82%. The yields of $CO_x$ (carbon monoxide and carbon dioxide) and acetic acid as byproducts were 9.73% and 2.13%, respectively.

Since a reaction in a reaction inhibition layer (inactive material layer) did not occur, an abnormal increase in temperature by a reduction in heat transfer efficiency was not observed.

Example 2

(Improved Heat Control System): Changes in Yield and Magnitudes of Temperature Peaks at Hot Spots with Change in Setting Temperature of Molten Salt This example was performed in the same manner as in Example 1 except for the setting temperatures of a molten salt in the second-stage reaction zone. The temperatures of the molten salt in the second-stage reaction zone were set to 280° C. and 270° C., respectively, in an axial direction.

In the second-stage reaction zone, the temperature at a hot spot was 325.5° C., and the yield of acrylic acid was 84.40%. The yields of $CO_x$ and acetic acid as byproducts were 9.90% and 1.95%, respectively.

$T_{h1}$-$T_{salt1}$ was 38.1° C., and $T_{h2}$-$T_{salt2}$ was 55.5° C.

Since a reaction in a reaction inhibition layer (inactive material layer) did not occur, an abnormal increase in temperature by a reduction in heat transfer efficiency was not observed.

Example 3

(Improved Heat Control System): Changes in Yield and Magnitudes of Temperature Peaks at Hot Spots with Change in Setting Temperature of Molten Salt This example was performed in the same manner as in Example 1 except for the setting temperatures of a molten salt and shear pressure in the second-stage reaction zone. The temperatures of the molten salt in the second-stage reaction zone were set to 280° C. and 270° C., respectively, in an axial direction, and the shear pressure was about 0.3 $kgf/cm^2G$.

In the second-stage reaction zone, the temperature at a hot spot was 335.2° C., and the yield of acrylic acid was 84.13%. The yields of $CO_x$ and acetic acid as byproducts were 8.46% and 1.91%, respectively.

$T_{h1}$-$T_{salt1}$ was 27.2° C., and $T_{h2}$-$T_{salt2}$ was 68.2° C.

Since a reaction in a reaction inhibition layer (inactive material layer) did not occur, an abnormal increase in temperature by a reduction in heat transfer efficiency was not observed.

Example 4

(A Case of the Use of Catalyst Layers with Slightly Different Activities

This Example was performed in the same manner as in Example 1 except for the filling structure of the catalysts and the setting temperature of molten salt.

The catalyst layers filled in the first-stage reaction zone were the same as in Example 1. In the second-stage reaction zone, different kinds of catalysts with slightly different activities were filled to heights of 700 mm at a first shell space and 1970 mm at a second shell space. The activities of the two catalysts were about 5% higher in the second shell space than in the first shell space. The temperatures of molten salt in the two shell spaces of the second-stage reaction zone were set to 275° C. and 270° C., respectively, in an axial direction.

In the second-stage reaction zone, the yield of acrylic acid was 83.38%. The yields of $CO_x$ and acetic acid as byproducts were 10.8% and 2.17%, respectively.

In the second-stage reaction zone, the temperature of a hot spot in the catalytic layer corresponding the first shell space was 321.9° C., and the temperature of a hot spot in the catalytic layer corresponding the second shell space was 313.5° C. $T_{h1}$-$T_{salt1}$ was 46.9° C., and $T_{h2}$-$T_{salt2}$ was 43.5° C.

Example 5

(A Case of the Use of Catalyst Layers with the Same Activity)

The first-stage reaction zone was filled with a catalyst layer of about 1200 mm, and the second-stage reaction zone was filled with catalyst layers of about 1100 mm. The catalysts filled in the second-stage reaction zone had the same activity, size and shape. The composition of a reaction mixture fed into the second-stage reaction zone was the same as in Example 1. The temperatures of molten salt in the two shell spaces of the second-stage reaction zone were set to 260° C. and 265° C., respectively, in an axial direction.

In the second-stage reaction zone, the yield of acrylic acid was 84.16%. The yields of $CO_x$ and acetic acid as byproducts were 8.11% and 1.80%, respectively.

In the second-stage reaction zone, the temperature of a hot spot in the catalytic layer corresponding the first shell space was 311.8° C., and the temperature of a hot spot in the catalytic layer corresponding the second shell space was 280.5° C. $T_{h1}$-$T_{salt1}$ was 51.8° C., and $T_{h2}$-$T_{salt2}$ was 15.5° C.

Example 6

(A Case of the Use of Catalyst Layers with the Same Activity)

Acrylic acid was produced in the same reaction conditions as in Example 5 except that the activity of catalysts in the second-stage reaction zone was 130% of the catalyst activity in Example 5.

In the second-stage reaction zone, the yield of acrylic acid was 83.17%. The yields of $CO_x$ and acetic acid as byproducts were 9.11% and 2.00%, respectively.

In the second-stage reaction zone, the temperature of a hot spot in the catalytic layer corresponding the first shell space was 333.1° C., and the temperature of a hot spot in the catalytic layer corresponding the second shell space was 329.5° C. $T_{h1}$-$T_{salt1}$ was 73.1° C., and $T_{h2}$-$T_{salt2}$ was 64.5° C.

Comparative Example 1

(The Case of Operations Under Isothermal Conditions Without the Application of a Multi-stage Heat Control System): Changes in Hot Spot Temperature and Yield with Change in Setting Temperature of Molten Salt Comparative Example 1 was performed in the same manner as in Example 1 except that the temperature of molten salt in the second-stage reaction zone was set to an isothermal temperature of 275° C.

In the second-stage reaction zone, the yield of acrylic acid was 83.30%. The yields of $CO_x$ and acetic acid as byproducts were 9.07% and 2.16%, respectively.

In the second-stage reaction zone which had been operated at isothermal conditions, the temperature of a hot spot was 353.9° C., and $T_{h1}$-$T_{salt1}$ was about 79° C.

Comparative Example 2

(The Case of Operations Under Isothermal Conditions Without the Application of a Multi-stage Heat Control System): the Use of Highly Active Catalysts with the Same Activity and Size Comparative Example 2 was performed in the same manner as in Example 6 except that the temperature of molten salt in the second-stage reaction zone was set to an isothermal temperature of 275° C.

In the second-stage reaction zone, the yield of acrylic acid was 82.83%. The yields of $CO_x$ and acetic acid as byproducts were 9.35% and 2.40%, respectively.

In the second-stage reaction zone which had been operated at isothermal conditions, the temperature of a hot spot was 410.1° C., and $T_{h1}$-$T_{salt1}$ was 135.1° C.

Comparative Example 3

(The Case Where a Multi-stage Heat Control System was Applied but Operation was Performed at Temperatures Out of the Limited Temperature Range): Changes in Hot Spot Temperature and Yield with Change in Setting Temperature of Molten Salt This Comparative Example was performed in the same manner as in Example 6 except that the second-stage reaction zone was divided into two shell spaces, and the temperatures of molten salt in the divided shell spaces were set to 275° C. and 280° C., respectively, in an axial direction.

In the second-stage reaction zone, the yield of acrylic acid was 81.87%. The yields of $CO_x$ and acetic acid as byproducts were 10.2% and 2.42%, respectively.

In a portion corresponding to the first shell space in the second-stage reaction zone, the peak temperature (the temperature at a hot spot) was 407.3° C., and in a portion corresponding to the second shell space, the peak temperature was 391.3° C. $T_{h1}$-$T_{salt1}$ was 132.3° C., and $T_{h2}$-$T_{salt2}$ was about 111.3° C.

Comparative Example 4

(A Case Where a Multi-stage Heat Control System Was Applied but the Thickness of a Reaction Inhibition Layer Was 10% of the Thickness of a Partition): Changes in Hot Spot Temperature and Yield with Change in Setting Temperature of Molten Salt The filling structure of the catalyst layers was the same as in Example 4, but the reaction inhibition layer used considering heat transfer in the location of the partition was inserted to a thickness corresponding to only about 10% of the partition thickness. The temperatures of molten salt in the second-stage reaction zone were set to 275° C. and 270° C. in an axial direction. The results of Example 4 and Comparative Example 4 are shown in Table 1 below for comparison.

Comparative Example 5

(A Case Where a Multi-stage Heat Control System Was Applied but a Reaction Inhibition Layer Was Not Used): Changes in Hot Spot Temperature and Yield With Change in Setting Temperature of Molten Salt)

Example 4 was repeated except that the reaction inhibition layer was not used. Heat transfer rate can be controlled by, for example, a method of controlling the circulation rate of molten salt. The temperatures of molten salt in the second-stage reaction zone were set to 275° C. and 270° C. in an axial direction. The results of Example 4 and Comparative Examples 4 and 5 are shown in Table 1 for comparison.

TABLE 1

| Reaction stage | Items | Example 4 | Comparative Example 4 | Comparative Example 5 |
|---|---|---|---|---|
| Second stage | Molten salt temperature (° C.) | 275 270 | 275 270 | 275 270 |
| | $T_{intf}$ (° C.) | 278.0 | 312.7 | 326.3 |
| | $T_{intf} - T_{salt1}$ (° C.) | 3.0 | 37.7 | 51.3 |
| | Acrylic acid yield | 84.82% | 83.02% | 82.91% |
| | $CO_x$ yield | 9.73% | 10.1% | 11.2% |
| | Acetic acid yield | 2.13% | 2.11% | 2.23% |

$T_{intf}$: The temperature of a catalyst layer at the position of a partition.

It could be found that $T_{h1}-T_{salt1}$ and $T_{h2}-T_{salt2}$ in Examples 1 to 4 were within limits of 130° C. and 110° C., and preferably 75° C. and 70° C., respectively, as proposed in the present invention. When Examples where the reaction inhibition layer had been introduced in the multi-stage heat control system and two or more catalyst layers had been used in the second-stage reaction region were compared to Comparative Examples, it could be found that the yield in Examples was always higher than that in Comparative Examples.

Particularly from the comparison of Example 1 to Comparative Example 1 conducted without the improved heat control system, the yield of acrylic acid, a final product, was about 1.5% higher in Example 1 than in Comparative Example 1.

And in Comparative Example 1, it could be found that $\Delta T$ ($T_h-T_{salt}$) exceeded 75° C., a preferred value proposed in the present invention, and the yield of acrylic acid, a final product, was about 1.5% lower than that in Example 1 due to increases in unreacted acrolein and byproducts, such as carbon dioxide and acetic acid.

In addition, in Comparative Example 2 using the highly active catalyst with reduced size, it could be found that $\Delta T$ ($T_h-T_{salt}$) exceeded 130° C., a limit proposed in the present invention, and the yield of acrylic acid was significantly reduced as compared to Example 6.

In Comparative Example 3 where the second-stage reaction zone had been divided into two reaction zones whose temperature setting had been changed in an axial direction, it could be found that $T_{h1}-T_{salt1}$ and $T_{h2}-T_{salt2}$ were not within limits of 130° C. and 110° C., respectively, as proposed in the present invention. Also, the yield of acrylic acid was reduced and the amount of byproduct $CO_x$ was 1% increased, as compared to Example 6.

Table 1 above shows the results of experiments conducted in order to solve the problem that heat transfer does not easily occur due to the insertion of the partition. In Example 4, the reaction inhibition layer was inserted into a location into which the partition has been placed. Comparative Example 4 was the same as in Example 4 except that the thickness of the reaction inhibition layer was 10% of the partition thickness. Comparative Example 5 was the same except that the reaction inhibition layer was not inserted into the location of the partition. As evident from Table 1, since it was not easy to control temperature at the partition location with the problem of heat transfer, Comparative Examples 4 and 5 showed temperature increases of 37.7° C. and 51.3° C., respectively, compared to the temperatures of molten salt, which are significantly different from that of Example 4. Particularly in Comparative Example 5, it could be found that $T_{intf}$ (the temperature of the catalyst layer at the partition location) was close to the peak temperature of the catalyst layer. It is believed that this is mainly attributed to heat accumulation by an exothermic reaction which occurs since heat transfer around the partition is not easy. If the reaction inhibition layer is not used, heat accumulation will not be the only problem. As apparent from Comparative Examples 4 and 5 where the reaction inhibition layer was not sufficiently ensured, the yield of acrylic acid, a final product, was also reduced as compared to Example 4. This indicates that reaction heat at the partition location did not easily flow out, so as to cause an abnormal increase in temperature and finally a reduction in selectivity, thus leading to an increase in the amount of byproducts.

In addition, the results of Example 5 where catalysts with the same catalyst activity had been used in the divided shell spaces also showed no problems of a hot spot and heat accumulation around the hot spot.

INDUSTRIAL APPLICABILITY

As described above, the present invention provides the improved heat control system for use in the two-stage process of producing unsaturated acids by the oxidation of olefins. This heat control system allows the design of a reactor system to which the advantages of the prior art can be sufficiently applied even under reaction conditions with high load. If this heat control system is used, the formation of a hot spot or heat accumulation in the hot spot can be inhibited, and as a result, unsaturated acids can be produced at high productivity and also the life cycle of a catalyst can be extended.

According to the present invention, the temperature difference between the peak temperature of the catalyst layer and the temperature of the heat transfer medium (molten salt) in each of the divided reaction zones is controlled, so that the catalyst can show relatively uniform activity in an axial direction. This can inhibit not only heat accumulation at a hot spot but also side reactions, thus preventing a reduction in yield.

Accordingly, the present invention can be stably performed at high reactant concentration or high reactant space velocity without controlling the activity of a catalyst filled in the second-stage reactor.

The invention claimed is:

1. In a process of producing unsaturated acids from unsaturated aldehydes by fixed-bed catalytic partial oxidation in a shell-and-tube heat exchanger-type reactor, the reactor comprising one or more catalytic tubes each including a reaction zone of producing the unsaturated acids, the improvement wherein:
the reaction zone is divided into two or more shell spaces by at least one partition,
each of the divided shell spaces being filled with a heat transfer medium, the heat transfer medium being maintained at isothermal temperature or a temperature difference of 0-5° C., and
when the shell spaces divided by the partition in the reaction zone are named, such as zone 1, zone 2, zone 3, . . . and zone N in an axial direction, $T_{h1}$-$T_{salt1}$ is $\leq 130°$ C. and $T_{hN}$-$T_{saltN}$ is $\leq 110°$ C., wherein N is an integer of 2 or more, $T_{h1}$ is the peak temperature of a reaction mixture in a catalyst layer corresponding to the first shell space, $T_{hN}$ is the peak temperature of a reaction mixture in a catalyst layer corresponding to the Nth shell space, $T_{salt1}$ is the temperature of a heat transfer medium filled in the first shell space, and $T_{saltN}$ is the temperature of a heat transfer medium filled in the Nth shell space.

2. The process of claim 1, which is a process of producing acrylic acid from an acrolein-containing gas mixture.

3. The process of claim 1, wherein the temperature difference between the heat transfer media filled in the adjacent shell spaces is in a range of 0° C.-50° C.

4. The process of claim 1, wherein the partition is disposed in such a manner that it covers at least one temperature peak.

5. The process of claim 4, wherein the temperature peak occurs at the inlet of the reactor, the front portion of the reaction zones, or a boundary between the adjacent catalyst layers with different activities.

6. The process of claim 1, wherein a reaction inhibition layer made of an inactive material alone or a mixture of the inactive material and a catalyst material is placed in a position within the catalytic tube, which corresponds to a position where the partition is disposed.

7. The process of claim 6, wherein the volume ratio of the inactive material to the catalyst material in the reaction inhibition layer is 20-100%.

8. The process of claims 6, wherein the filling height of the reaction inhibition layer is 20-500% of the thickness of the partition.

9. The process of claim 1, wherein the temperatures of the heat transfer medium filled in each of the shell spaces can be controlled independently.

10. The process of claim 1, wherein the space velocity of the unsaturated aldehydes introduced into the reactor inlet is in a range of 50-130 hr$^{-1}$.

11. In a process of producing unsaturated acids from unsaturated aldehydes by fixed-bed catalytic partial oxidation in a shell-and-tube heat exchanger-type reactor, the reactor comprising one or more catalytic tubes each including a reaction zone of producing the unsaturated acids, the improvement wherein:
the reaction zone is divided into two or more shell spaces by at least one partition,
each of the divided shell spaces being filled with a heat transfer medium, the heat transfer medium being maintained at isothermal temperature or a temperature difference of 0-5° C.,
in which a reaction inhibition layer made of an inactive material alone or a mixture of the inactive material and a catalyst material is placed in a position within the catalytic tube, which corresponds to a position where the partition is disposed.

12. The process of claim 11, which is a process of producing acrylic acid from an acrolein-containing gas mixture.

13. The process of claim 11, wherein the temperature difference between the heat transfer media filled in the adjacent shell spaces is in a range of 0° C.-50° C.

14. The process of claim 11, wherein the partition is disposed in such a manner that it covers at least one temperature peak.

15. The process of claim 14, wherein the temperature peak occurs at the inlet of the reactor, the front portion of the reaction zones, or a boundary between the adjacent catalyst layers with different activities.

16. The process of claim 11, wherein the volume ratio of the inactive material to the catalyst material in the reaction inhibition layer is 20-100%.

17. The process of claims 11, wherein the filling height of the reaction inhibition layer is 20-500% of the thickness of the partition.

18. The process of claim 11, wherein the temperatures of the heat transfer medium filled in each of the shell spaces can be controlled independently.

19. The process of claim 11, wherein the space velocity of the unsaturated aldehydes introduced into the reactor inlet is in a range of 50-130 hr$^{-1}$.

20. In a shell-and-tube heat exchanger-type reactor which can be used in a process of producing unsaturated acids from olefins by fixed-bed catalytic partial oxidation, the reactor comprising one or more catalytic tubes each including a first-stage reaction zone of mainly producing unsaturated aldehydes, a second-stage reaction zone of mainly producing unsaturated acids, or both the two reaction zones, the improvement wherein: the second-stage reaction zone is divided into two or more shell spaces by at least one partition, each of the divided shell spaces being filled with a heat transfer medium, the heat transfer medium in each of the shell spaces being maintained at isothermal temperature or a temperature difference of 0-5° C., and when the shell spaces divided by the partition in the second-stage reaction zone are named, such as zone 1, zone 2, zone 3, . . . and zone N in an axial direction, $T_{h1}$-$T_{salt1}$ is $\leq 130°$ C. and $T_{hN}$-$T_{saltN}$ is $\leq 110°$ C., wherein N is an integer of 2 or more, $T_{h1}$ is the peak temperature of a reaction mixture in a catalyst layer corresponding to the first shell space , $T_{hN}$ is the peak temperature of a reaction mixture in a catalyst layer corresponding to the Nth shell space, $T_{salt1}$ is the temperature of a heat transfer medium filled in the first shell space, and $T_{saltN}$ is the temperature of a heat transfer medium filled in the Nth shell space.

21. In a shell-and-tube heat exchanger-type reactor which can be used in a process of producing unsaturated acids from olefins by fixed-bed catalytic partial oxidation, the reactor comprising one or more catalytic tubes each including a first-stage reaction zone of mainly producing unsaturated aldehydes, a second-stage reaction zone of mainly producing unsaturated acids, or both the two reaction zones, the improvement wherein: the second-stage reaction zone is divided into two or more shell spaces by at least one partition, each of the divided shell spaces being filled with a heat transfer medium, the heat transfer media being maintained at isothermal temperature or a temperature difference of 0-5° C., in which a reaction inhibition layer made of an inactive material alone or a mixture of the inactive material and a catalyst is placed within a portion of the catalytic tube, which corresponds to a location where the partition is disposed.

* * * * *